United States Patent
Bollenbeck (10) Patent No.: US 9,985,776 B2
(45) Date of Patent: May 29, 2018

(54) COMMUNICATION METHOD, COMMUNICATION DEVICE AND MAGNETIC RESONANCE TOMOGRAPHY SYSTEM WITH COMMUNICATION DEVICE

(71) Applicant: Jan Bollenbeck, Eggolsheim (DE)

(72) Inventor: Jan Bollenbeck, Eggolsheim (DE)

(73) Assignee: Siemens Aktiengesellschaft, München (DE)

( * ) Notice: Subject to any disclaimer, the term of this patent is extended or adjusted under 35 U.S.C. 154(b) by 501 days.

(21) Appl. No.: 14/631,480

(22) Filed: Feb. 25, 2015

(65) Prior Publication Data
US 2015/0244515 A1   Aug. 27, 2015

(30) Foreign Application Priority Data
Feb. 25, 2014   (DE) .......... 10 2014 203 368

(51) Int. Cl.
*H04L 27/14*   (2006.01)
*H04L 7/033*   (2006.01)
(Continued)

(52) U.S. Cl.
CPC .......... *H04L 7/0331* (2013.01); *G01R 33/283* (2013.01); *G01R 33/543* (2013.01);
(Continued)

(58) Field of Classification Search
CPC ......... H04L 27/14; H04L 27/12; H04L 27/20; H04L 27/22; H04L 27/18; H04L 7/0331; G01R 33/543; G01R 33/20
(Continued)

(56) References Cited

U.S. PATENT DOCUMENTS

| 5,317,315 A | 5/1994 | Karhunen et al. |
| 2005/0078743 A1* | 4/2005 | Shohara ................ H03J 7/04 375/219 |

(Continued)

FOREIGN PATENT DOCUMENTS

| CN | 101789859 A | 7/2010 |
| CN | 102215200 A | 10/2011 |

(Continued)

OTHER PUBLICATIONS

Korean office Action for related Korean Application No. 10-2015-0026672 dated Oct. 19, 2015, with English Translation.
(Continued)

*Primary Examiner* — Michael Neff
(74) *Attorney, Agent, or Firm* — Lempia Summerfield Katz LLC (57) ABSTRACT

A communication method for communication between a first and a second communication apparatus, where at least one wanted signal is transmitted from the second communication apparatus to the first communication apparatus is provided. The method includes sending a first carrier signal at a first frequency using the first communication apparatus. The method also includes receiving the first carrier signal using the second communication apparatus and generating a second carrier signal at a second frequency. The method includes changing the second frequency and/or a specified phase angle, and/or modulating the second carrier signal in each case as a function of the wanted signal in order to generate a transmit signal. The transmit signal is sent by the second communication apparatus, and the transmit signal is received and demodulated in order to recover the wanted signal using the first communication apparatus.

23 Claims, 4 Drawing Sheets (51) Int. Cl.
- *G01R 33/28* (2006.01)
- *G01R 33/54* (2006.01)
- *H02J 7/00* (2006.01)
- *H04L 27/12* (2006.01)
- *H04L 27/20* (2006.01)
- *H04L 27/22* (2006.01)
- *A61B 5/055* (2006.01)

(52) U.S. Cl.
CPC ............ *H02J 7/0044* (2013.01); *H04L 27/12* (2013.01); *H04L 27/14* (2013.01); *H04L 27/20* (2013.01); *H04L 27/22* (2013.01); *A61B 5/055* (2013.01)

(58) Field of Classification Search
USPC .......................................................... 375/268
See application file for complete search history.

(56) References Cited

U.S. PATENT DOCUMENTS

2010/0277360 A1* 11/2010 Lee ..................... G01S 5/0289
342/125

2012/0146834 A1* 6/2012 Karr ...................... G01S 13/325
342/47
2015/0220763 A1 8/2015 Porzelt
2015/0382346 A1 12/2015 Khandekar et al.

FOREIGN PATENT DOCUMENTS

| | | |
|---|---|---|
| DE | 4302394 A1 | 8/1993 |
| DE | 102014201931 A1 | 8/2015 |
| JP | H0541675 A | 2/1993 |
| JP | H08294065 A | 11/1996 |
| KR | 20120038009 A | 4/2012 |
| WO | WO2011072667 A1 | 6/2011 |

OTHER PUBLICATIONS

Floyd, M. Gardner; "Phaselock Techniques", Second Edition, John Wiley & Sons, 1979.
Frequency divider, in: http://en.wikipedia.org/wiki/Frequency_divider, Apr. 1, 2013.
German Office Action for related German Application No. 10 2014 203 368.3, dated Jan. 30, 2015, with English Translation.
Chinese Office Action for Chinese Patent Application No. 201510082073.4, dated Aug. 31, 2017, with English Translation.

* cited by examiner

FIG 5

COMMUNICATION METHOD, COMMUNICATION DEVICE AND MAGNETIC RESONANCE TOMOGRAPHY SYSTEM WITH COMMUNICATION DEVICE

This application claims the benefit of DE 10 2014 203 368.3, filed on Feb. 25, 2014, which is hereby incorporated by reference in its entirety.

BACKGROUND

The present embodiments relate to communication between a first and a second communication apparatus.

While undergoing an examination in a magnetic resonance tomography system, a patient may be positioned in a narrow tube. The patient is to remain motionless and is exposed to high levels of noise. For example, in order to avoid inducing states of anxiety in a patient, to offer the patient a way of communicating and to allow instructions to be passed to the patient, it is desirable to be able to communicate with the patient during an examination. For this purpose, pneumatically driven communication systems in which acoustic information is transmitted to a patient headset by air pressure modulation are used. To enable communication in the reverse direction, a pneumatically driven squeeze bulb is provided for the patient, and hand microphones are arranged at the ends of the tube.

Owing to the use of a pneumatic system for the acoustic transmission or for transmitting the signals of the squeeze bulb, compressed air tubes are to be installed in the magnetic resonance tomography system, which complicates the handling of the magnetic resonance tomography system. Transmitting sound via compressed air tubing limits the attainable transmission quality. The use of pneumatic squeeze bulbs does not represent an ideal solution, since actuating a pneumatic squeeze bulb requires a relatively large force, which is problematic for some patients.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an improved communication method suitable for patient communication in a magnetic resonance tomography system and that has low susceptibility to interference is provided.

A communication method includes sending a first carrier signal at a first frequency using a first communication apparatus, receiving the first carrier signal by the second communication apparatus, and generating a second carrier signal at a second frequency. The second frequency is different from the first frequency and has a specified rational frequency ratio with respect to the first frequency and a specified phase angle to the phase of the first carrier signal. The communication method also includes changing the second frequency and/or the specified phase angle, and/or modulating the second carrier signal in each case as a function of a wanted signal in order to generate a transmit signal, and sending the transmit signal by the second communication apparatus. The transmit signal is received and demodulated in order to recover the wanted signal using the first communication apparatus.

A phase-locked transponder is used in the second communication apparatus. A phase-locked transponder signal is not sent directly, but in addition, is modulated by a wanted signal. Using a constant sending of the first carrier signal as well as of the transmit signal, disturbances to the connection may be detected instantly. The second carrier signal is phase-locked for receiving the first carrier signal. Therefore, provided the relative speed between the communication apparatuses is not too great, the phase angle of the transmit signal received in the first communication apparatus relative to the first carrier signal is, with the exception of a constant phase shift dictated by the signal propagation delay between the first and the second communication apparatus, exclusively dependent on the wanted signal. What this achieves, in comparison with an independent generation of the first carrier signal and the second carrier signal, is a high frequency and phase stability, and consequently, an overall improvement in the transmission of the wanted signal, with little potential to interfere with the MR imaging (e.g., when a clock signal used to generate the first carrier signal is also used in the course of the demodulation).

In order to transmit the wanted signal, a phase modulation or a frequency modulation of the second carrier signal by the wanted signal, for example, may be used. For example, with analog wanted signals, a modulation may be carried out directly using the wanted signal, which is, for example, preamplified or attenuated. This enables, for example, acoustic signals, such as the voice of a patient, to be transmitted. Digital signals, for example, may also be transmitted by a change in the phase angle of the second carrier signal. In order to avoid phase jumps in the transmit signal and a wideband transmit signal associated therewith, the phase changes may be generated by signal inversions in the course of the generation of the second carrier signal.

In this case, the second frequency of the second carrier signal may, for example, be smaller than the first frequency of the first carrier signal. The second frequency is neither an integer multiple nor an integer divisor of the first frequency. The problem that higher harmonic oscillations of the first carrier signal will interfere with the second carrier signal, or vice versa, is avoided.

When the communication method according to one or more of the present embodiments is used for patient communication in a magnetic resonance tomography system, for example, the second communication apparatus is assigned to the patient. In addition, for use in the magnetic resonance tomography system, both the first and the second frequency may lie below or close to the 1 H magnetic resonance frequency. The first frequency and the second frequency may be chosen, for example, so that the first frequency and the second frequency lie in a magnetic-field-dependent grid in which no magnetic resonance signals are expected. For example, frequencies that are a multiple of 2.5 megahertz (e.g., 25 megahertz and 20 megahertz) may be used in this case as the first and second frequencies.

In addition, a further wanted signal may be modulated onto the first carrier signal by the first communication apparatus. For example, a phase modulation or a frequency modulation may be used in this case for modulating the wanted signal onto the carrier signal, in which event, for example, wanted signals without a constant signal component may be used, or the wanted signals may be high-pass filtered. If a demodulation is carried out in the second communication apparatus, for example, using a phase-locked loop circuit having a small bandwidth, then an oscillator of the phase-locked loop circuit tracks the average value of the frequency of the received signal, and consequently, the first frequency of the first carrier signal. The oscillator therefore makes a signal that is phase-locked to the unmodulated first carrier signal available. In such an embodiment of the second communication apparatus, the further wanted signal may be tapped upstream of a loop filter of the phase-locked loop circuit.

In the communication method according to one or more of the present embodiments, the first communication apparatus is intended to communicate with a plurality of further communication apparatuses. For example, when the communication method according to one or more of the present embodiments is used for patient communication in a magnetic resonance tomography system, the signal may also be transmitted by the communication method to a further device (e.g., an electrocardiograph). A third communication apparatus may therefore receive the first carrier signal and generate a third carrier signal at a third frequency. The third frequency is different from the first frequency and the second frequency and has a specified rational frequency ratio with respect to the first frequency as well as a specified phase angle to the phase of the first carrier signal. Thereafter, the third frequency and/or the specified phase angle of the third carrier signal may be varied as a function of a third wanted signal, and/or the third carrier signal may be modulated by the third communication apparatus. As a result of using a common first carrier signal for the second communication apparatus and the third communication apparatus, for example, the use of an additional frequency range for communication is avoided.

For example, a voice input may be acquired as the wanted signal by the second communication apparatus and transmitted to the first communication apparatus, where the voice input is output at the first communication apparatus using a sound converter.

As will be explained in greater detail below, rational and non-integer frequency ratios may be generated (e.g., using a combination of a phase-locked loop circuit with a mixer). For the purpose of generating the second carrier signal, the ability of phase-locked loop circuits to regulate an oscillator of the phase-locked loop circuit also to frequencies that are harmonics or subharmonics of an input signal may be used. For example, a communication apparatus having a phase-locked loop circuit for generating the second carrier signal may therefore be used as the second communication apparatus. The first frequency is chosen such that in the locked state of the phase-locked loop circuit, a feedback signal supplied to a first input of a phase detector of the phase-locked loop circuit has a fourth frequency that is, for example, an odd integer multiple (1, 3, 5, . . . ) or, for example, an odd integer divisor (1/1, 1/3, 1/5, . . . ) of a fifth frequency of an input signal at a second input of the phase detector. The fourth frequency or the fifth frequency may be equal to the first frequency, the second frequency, or the third frequency or be different from the frequencies.

A stable regulation of the phase of an oscillator of the phase-locked loop circuit with respect to the phase of an input signal may also be provided using the phase detector, for example, when a frequency ratio of three, five, seven, and so forth, is present between the two input signals of the phase detector. An appropriate choice of the frequency of the first carrier signal and the use of bandpass filters and/or the use of an oscillator that is tunable only over a relatively narrow frequency range accordingly enables a frequency division to be carried out by the phase detector. For example, the fourth frequency may be three times as large as the fifth frequency.

In addition, one or more of the present embodiments relate to a communication device, for example, for patient communication in a magnetic resonance tomography system. The communication device includes a first communication apparatus and a second communication apparatus. The first communication apparatus includes a transmit device for sending a carrier signal at a first frequency, a receive device for receiving a transmit signal of the second communication apparatus, and a demodulation device for recovering a wanted signal from the transmit signal. The second communication apparatus includes a receive antenna for receiving the first carrier signal and a transmit antenna for sending the transmit signal by a second carrier signal that has a second frequency that is different from the first frequency. The second communication apparatus includes a mixer, a filter and a phase-locked loop circuit. The mixer may be supplied with the receive signal and an output signal of the phase-locked loop circuit, and an output signal of the mixer may be supplied to an input of the phase-locked loop circuit via the filter. The output signal of the phase-locked loop circuit is the second carrier signal and stands in a rational frequency ratio and a specified phase relationship to the first carrier signal. The second communication apparatus includes a modulation circuit that modulates the second carrier signal as a function of a wanted signal in order to generate the transmit signal.

In one embodiment, a transmit signal is sent by a second carrier signal that is phase-locked to a reference source (e.g., the first carrier signal). In order to prevent the first carrier signal from interfering with the second carrier signal, selecting the first frequency as an integer multiple or an integer divisor of the second frequency may be avoided. Accordingly, simple transponders having frequency dividers such as transponders based, for example, on a Miller frequency divider may not be used. According to one or more of the present embodiments, a frequency-converting, phase-locked transponder that outputs the second carrier signal is provided in the second communication apparatus through the use of a mixer and a phase-locked loop circuit. The frequency ratio may be defined, for example, by frequency dividers in the circuit. It is, however, also possible for frequency division purposes to make use of the fact that phase-locked loop circuits may also generate harmonic or subharmonic signals of an input signal. For example, digital counters may be provided in this case for the frequency division.

The described supplying of signals to the components may be effected in each case by a direct electrically conductive connection (e.g., a conductor track). However, the signals may also be supplied indirectly via other components. In this case, amplifiers (e.g., non-linear amplifiers having soft saturation), further filters (e.g., bandpass filters at the first frequency and/or at the second frequency or at an intermediate frequency that a signal has downstream of the mixer), comparators for converting the signal into a pulse wave (e.g., Schmitt triggers), frequency multipliers, and frequency dividers (e.g., digital counters) may be provided in the signal path.

A frequency divider may be connected, for example, into a feedback circuit of the phase-locked loop circuit and/or upstream of the input of the phase-locked loop circuit and/or between the output of the phase-locked loop circuit and the mixer. In an arrangement of the frequency divider in the feedback circuit, the output signal of the frequency divider may also be supplied, for example, to the mixer, with the non-frequency-divided signal continuing to be used as the carrier signal. Frequency multipliers may also be used instead of frequency dividers. This results in a further degree of freedom in the formulation of the frequency plan.

For example, a non-linear amplifier may be connected between the receive antenna and the mixer and/or between the mixer and the phase-locked loop circuit. In the communication device according to one or more of the present embodiments, only the phases or frequencies of signals may be evaluated both for the purpose of generating the second carrier signal and for the communication of user data. In the case of a non-linear amplification, however, no information loss occurs in an exclusive evaluation of the phase or frequency of the signal. A particularly simple, favorable and efficient amplification may be achieved by non-linear amplifiers. A bandpass filter may be arranged upstream of and/or downstream of a non-linear amplifier.

The phase-locked loop circuit may include, for example, a phase detector, a loop filter and an oscillator. The oscillator may be a crystal oscillator that is adjustable by a regulating voltage (e.g., voltage-controlled xtal (crystal) oscillator (VCXO)). Crystal oscillators may output oscillations having a very stable frequency with respect to time. Voltage-controlled crystal oscillators may be adjustable in a relatively narrowband frequency range (e.g., 100 ppm; an adjustment width of 1 kilohertz at an oscillation frequency of 10 megahertz). This bandwidth is sufficient to achieve a locking of the oscillator phase and consequently a phase-lock of the second carrier signal to the first carrier signal. At the same time it is, however, provided by the relatively narrow frequency range that the oscillator does not oscillate at a harmonic or subharmonic frequency of the desired frequency.

The frequency of the oscillator is specified or adjustment is effected by the output signal of the loop filter, which is embodied, for example, as an active integrator. By suitable choice of the reference voltage of the integrator, the operating point of the phase detector may be placed in the center point of the partially point-symmetrically extending phase detector characteristic curve in order to enable a bipolar modulation with a maximum phase deviation. In this case, the loop filter may be embodied, for example, such that the loop bandwidth of the phase-locked loop circuit is less than 100 hertz. What is achieved, for example, by this is that even in the case of a phase or frequency modulation of the first carrier signal, the oscillator of the phase-locked loop circuit is phase-locked to the unmodulated first carrier signal.

The phase detector may be embodied, for example, as an exclusive-OR gate. In this case, a comparator may be provided at the input and/or in the feedback path of the phase-locked loop circuit.

A transmit mode of operation by the second communication apparatus may take place only when the second carrier signal is phase-locked to the first carrier signal. The output signal of the loop filter may be supplied to a comparator having an output signal that triggers the output of the transmit signal. In a locked state of the phase-locked loop circuit, a constant regulating voltage that determines the frequency of the oscillator signal is present at the output of the loop filter. A locked state may therefore be recognized by the fact that the output signal of the loop filter is in a specified window around a specified value. The comparator switches to an on-state and activates the output of the transmit signal. In addition, an indicator device (e.g., a lamp) that indicates a locked state may be provided. This may likewise be controlled as described above.

In the communication device according to one or more of the present embodiments, digital signals may be transmitted, for example, by phase jumps of the second carrier signal. In order at the same time to keep the bandwidth of the signal small, the phase jumps may be generated by a phase adjustment in the course of the generation of the second carrier signal. An inverter that is switched as a function of the wanted signal may therefore be connected between the output of the oscillator and the mixer and/or between the output of the oscillator and the phase detector, and/or between the mixer and an input of the phase-locked loop circuit. For example, when frequency dividers are used in the course of the generation of the second carrier signal, inverting the signal at different points leads to different phase changes. Inverters may therefore be provided, for example, at a plurality of the points. As a result of this, up to eight different phase shifts may be generated when three inverters are used, for example. The phase jump may be filtered by the phase-locked loop circuit having a relatively small bandwidth, thereby avoiding a broadband spectrum of the transmit signal. Alternatively, a digital phase shift method may be used within the framework of the generation of the second carrier signal (e.g., using a digital signal delay).

The first carrier signal may be modulated prior to the transmission in order to transmit further user information to the second communication apparatus. The output signal of the phase detector may be supplied directly or indirectly to a sound converter. A demodulation is simultaneously carried out in the course of the generation of the second carrier signal in order to recover the further wanted signal. A loop filter having a very small bandwidth may be used, and the output signal of the phase detector is supplied to the sound converter, for example, via a lowpass filter and/or an amplifier.

The modulation circuit of the second communication apparatus may be, for example, a frequency or phase modulation circuit. For example, an analog wanted signal (e.g., a signal of a microphone) may be supplied as the modulation signal for a frequency or phase modulation. For the purpose of the communication of a further wanted signal from the first communication apparatus to the second communication apparatus, the first communication apparatus may also include, for example, a frequency or phase modulation circuit.

The second communication apparatus may include a rechargeable energy storage device for supplying energy and a charging device for charging the energy storage device using energy of the receive signal. This is advantageous, for example, when the second communication apparatus is mobile (e.g., when the second communication apparatus is assigned to a patient when used in a magnetic resonance tomography system). In addition, the first communication apparatus may include a charging device for receiving the second communication apparatus, and a transmit power control device that increases the transmit power of the first carrier signal when the second communication apparatus is received in the charging device. For example, the charging device may be embodied such that when the second communication apparatus is received in the charging device, the receive antenna of the second communication apparatus is magnetically strongly coupled to the transmit antenna of the first communication apparatus. A particularly large transfer of energy may take place from the first communication apparatus to the second communication apparatus. During this process, the transmit power control device may determine, for example, the increase in the load at the transmit antenna as a result of the larger energy transfer, and upon determining such a load increase, may increase the transmit power in order to achieve a particularly large transfer of energy during the charging process.

For example, when the communication device is used in conjunction with a magnetic resonance tomography system, the second communication apparatus may include a magnetic field detector (e.g., a Hall probe) for detecting a magnetic field. A transmission of the transmit signal is switchable as a function of a detected magnetic field. For this purpose, a comparator, for example, may be provided at an output of the magnetic field detector in order to trigger the sending of the transmit signal (e.g., by actuation of a switch, transistor or amplifier) as a function of an output signal of the magnetic field detector. What is achieved thereby, for example, is that the second communication apparatus is, for example, activated only when the second communication apparatus is in the tube of a magnetic resonance tomography system. As a result, interference due to unused second communication apparatuses may be avoided. When such apparatuses are not used, the energy consumption of the second communication apparatus may be reduced, and for example, an operating time of an energy store of the second communication apparatus may be extended.

A control device of the second communication apparatus may send a stored identification signal as a wanted signal when an identification condition occurs. The identification condition may be, for example, a triggering of the transmission of the transmit signal, a control input, or a predetermined further wanted signal received from the first communication apparatus. The identification signal may be sent as a digital signal. The transmission being is possible, for example, as a result of switching one or more of the above-described inverters.

In addition, one or more of the present embodiments relate to a magnetic resonance tomography system that includes a communication device, as described above and below. The communication device serves, for example, for patient communication. The second communication apparatus is mobile and is assigned to the patient. The voice of the patient and the actuation of a control element (e.g., a nurse call device) may be transmitted as the wanted signal to the first communication apparatus. For example, a microphone is provided at the second communication apparatus for the purpose of detecting voice inputs. The microphone signal is supplied as a modulation signal to a modulation circuit that modulates the second carrier signal. For example, one of the described inverters is controlled by the control element. In addition, voice or audio signal transmission to the patient is provided. The voice signal modulates (e.g., phase-modulates) the first carrier signal.

Features of the communication method, the communication device, and the magnetic resonance tomography system may be combined.

DETAILED DESCRIPTION

Figure 1:
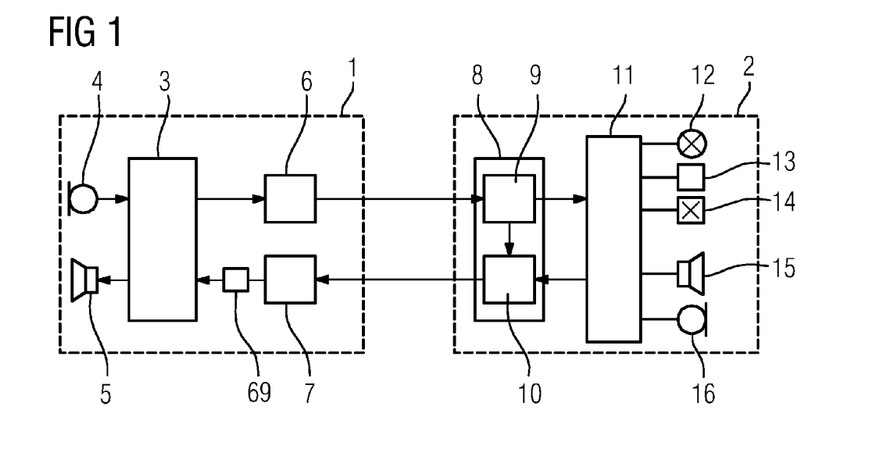
FIG. 1 shows a first embodiment of a communication device.

FIG. 1 shows an exemplary embodiment of a communication device having a first communication apparatus 1 and a second communication apparatus 2. The communication device is used for communication in a magnetic resonance tomography system. In this arrangement, the communication apparatus 1 is a stationary communication apparatus that is integrated into a control unit of the magnetic resonance tomography system and is assigned to an operator of the magnetic resonance tomography system. The communication apparatus 2 is mobile and assigned to the patient. The communication apparatus 2 is supplied with energy by a battery (not shown) that may be charged by the energy of the carrier signal transmitted by the first communication apparatus.

In this arrangement, the communication apparatus 1 includes a first control device 3 that serves for data input and output and controls the other components. The first control device 3 captures audio signals of a microphone 4 and is able to drive a loudspeaker 5 by audio signals. Voice input and output for communication between operating staff and the patient may be provided by the microphone 4 and the loudspeaker 5.

The communication with the second communication apparatus 2 is provided via a first transmit device 6 and a first receive device 7. A first carrier signal is generated by a crystal oscillator (not shown) in the first transmit device 6. The crystal oscillator is controllable as a function of voltage and is coupled, via a phase-locked loop circuit, to the phase of a reference signal provided by the first control device 3. A 10-megahertz reference signal is used, and the first carrier signal has a frequency of 30 megahertz. The signal detected by the microphone 4 is also supplied to the first transmit device 6 as an analog signal, by which the first carrier signal is phase-modulated in a modulation device of the first transmit device 6. The phase-modulated first carrier signal is sent via a transmit antenna (not shown).

The first receive device 7 receives the transmit signal sent by the second communication apparatus 2 and supplies the transmit signal to the demodulation device 69. The demodulation device 69 demodulates the signal in order to recover the wanted signal sent by the second communication apparatus 2. The basic design of a demodulation device 69 for demodulating a frequency or phase modulation is well known in the prior art. During the demodulation, use is made of the knowledge that the transmit signal of the communication apparatus 2 is based on a second carrier signal that is phase-locked to the first carrier signal and consequently also to the reference signal. Because all of the relevant phases and frequencies that are used within the framework of the communication are coupled to the first carrier signal, and consequently to the reference signal, a defined and stable second carrier frequency, and consequently a particularly interference-resistant communication, is achieved. For example, a drifting of the frequencies and relative phases of the signal sources used for modulation or demodulation in the communication device may be avoided, and consequently, the introduction of additional phase noise as well as the risk of disturbances in the MR imaging may also be avoided.

The second receive device 9 and the second transmit device 10 of the second communication apparatus 2 are formed by the phase-locked, frequency-converting transponder 8, which generates the second carrier signal serving to transport the wanted signal as a function of the first carrier signal. The layout of the transponder 8 is explained in detail with reference to FIGS. 2 and 3.

In addition, the second communication apparatus 2 includes a second control device 11 that serves, for example, for communication between the transponder 8 and the other elements of the second communication apparatus 2. The second communication apparatus 2 includes a microphone 16 and a loudspeaker 15 for voice communication, a Hall sensor 14, a control element 13 (e.g., a call button) and a lamp 12. The lamp is activated when the phase-locked loop circuit of the transponder 8 is locked (e.g., when a fixed phase relationship is present between the first and the second carrier signal). An inverter in the transponder 8 is activated by an actuation of the control element 13. As a result of this, as will be explained in greater detail with reference to FIG. 3, the phase of the second carrier signal is shifted by a defined amount relative to the phase of the first carrier signal. In this way, an actuation of the control element 13 may be detected by the first communication apparatus 1. At the same time, upon an actuation of the control element 13 being detected, a warning tone is output on the loudspeaker 5 by the first control device 3.

A magnetic field flowing through the Hall sensor 14 is detected by the Hall sensor 14. Provided in the second control device 11 is a comparator that switches an amplifier of the transponder 8 in order to activate the transmit mode of operation when the sensor data of the Hall sensor 14 is exceeded.

When the transmit mode of operation is initiated by the second communication apparatus 2, and at regular intervals during the transmit mode of operation, the second control device 11 is configured to transmit digital identification information stored in the second control device 11 to the first communication apparatus 1 by switching an inverter in the transponder 8 using a pattern corresponding to the identification information. In this way, it may be recognized when a plurality of second communication apparatuses 2 are active or which second communication apparatuses 2 are currently active.

Figure 2:
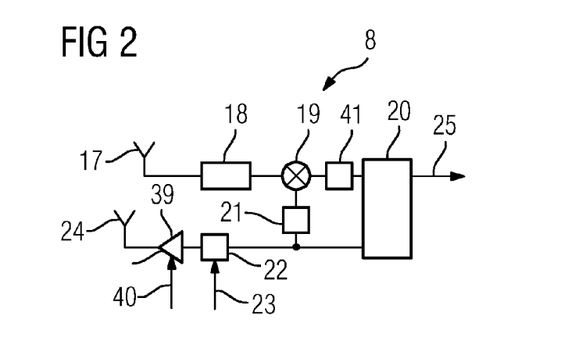
FIG. 2 shows one embodiment of a transponder of a second communication apparatus of the communication device shown in FIG. 1.

FIG. 2 schematically depicts the layout of the transponder 8. The first carrier signal sent by the communication apparatus 1 and modulated by a further wanted signal is received by the receive antenna 17 and amplified and filtered by a non-linear amplifier 18. The amplified and filtered signal is supplied to the mixer 19, by which a higher-frequency and a lower-frequency sideband are generated by multiplicative mixing with a further signal in each case. As a result of a subsequent filtering by the filter 41, which is embodied as a lowpass filter, the lower-frequency sideband is thereby supplied to the phase-locked loop circuit 20. Accordingly, the mixer 19 and the lowpass filter 41 essentially form a frequency converter that generates a signal having an intermediate frequency that lies lower by the frequency of the signal additionally supplied to the mixer 19 than the frequency of the first carrier signal.

The output signal of the filter 41 is supplied to the phase-locked loop circuit 20. The phase-locked loop circuit 20 will be explained in more detail hereinbelow with reference to FIG. 3. The phase-locked loop circuit 20 demodulates the signal received by the receive antenna 17 so that a further wanted signal that has been modulated onto the first carrier signal in the first communication apparatus may be routed via the output 25 to the second control device 11 and then may be output via the loudspeaker 15. The phase-locked loop circuit 20 includes an oscillator having a frequency that stands in a specified frequency ratio to a frequency at the input of the phase-locked loop circuit and that is phase-locked to said input signal. The phase-locked loop circuit 20 has a very small loop bandwidth. As a result of this, the oscillator of the phase-locked loop circuit 20 does not track the modulation of the first carrier signal, but is phase-locked to the unmodulated first carrier signal.

The oscillator signal of the phase-locked loop circuit 20 is supplied to the mixer 19 via a frequency divider 21, and to a modulation circuit 22. The phase-locked loop circuit 20 accordingly provides the second carrier signal, which stands in a fixed phase relationship to the first carrier signal. The phase-locked loop circuit 20 includes frequency dividers neither at an input nor in a feedback loop. The frequency of the second carrier signal is accordingly dependent exclusively on the division factor of the frequency divider 21. The frequency of the intermediate signal downstream of the filter 41 is equal to the difference between the frequency of the first carrier signal and the frequency of the second carrier signal, divided by the division factor of the frequency divider 21. The division factor of the frequency divider 21 is two. Accordingly, the frequency of the second carrier signal is ⅔ of the frequency of the first carrier signal. The first communication apparatus 1 sends a carrier signal at 30 megahertz. The second communication apparatus 2 therefore sends a transmit signal at a second carrier frequency of 20 megahertz. If, alternatively, a different division factor k is specified for the frequency divider 21, then the ratio of the second carrier frequency to the first carrier frequency is $F2/F1=k/(k+1)$.

The carrier signal is frequency-modulated by the modulation circuit 22 using a signal specified at the input 23. A preprocessed voice signal recorded by the microphone 16 is fed in at the input 23 by the second control device 11. Accordingly, a wanted signal is also modulated onto the second carrier signal in the modulation circuit 22 in order to generate a transmit signal. The transmit signal is supplied to the transmit antenna 24. The amplifier 39, which is controlled by the control signal 40, is connected between the modulation circuit 22 and the transmit antenna 24. The amplifier 39 is controlled by the second control device 11 as a function of whether the first and the second carrier signal are currently phase-locked. The amplifier 39 is activated by the control signal 40 only if a minimum magnetic field is registered at the Hall sensor 14.

Figure 3:
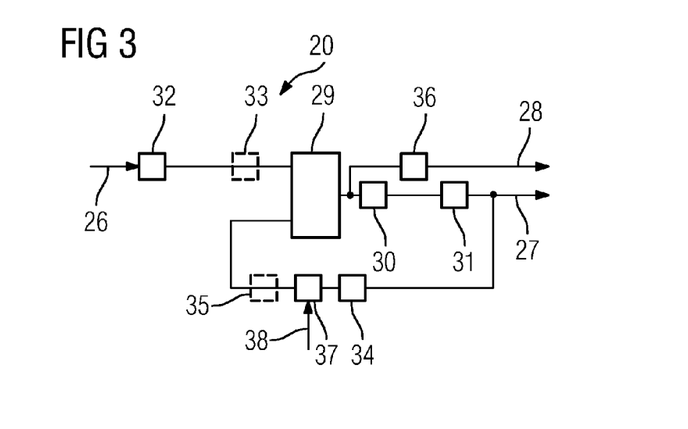
FIG. 3 shows one embodiment of a phase-locked loop circuit of the transponder shown in FIG. 2.

FIG. 3 schematically depicts the layout of the phase-locked loop circuit 20 from FIG. 2. The output signal of the filter 41 is supplied to the phase-locked loop circuit 20 via the input 26. The phase-locked loop circuit provides two output signals 27, 28, where the output signal 27 is the second carrier signal that is supplied to the frequency divider 21 and the modulation circuit 22, and the output signal 28 is forwarded as signal 25 to the second control device 11. The output signal 28 serves for driving the loudspeaker 15.

The incoming signal at the input 26 is converted by the comparator 32, a Schmitt trigger, into a square wave. In a development of the illustrated communication device, a frequency divider 33 may be arranged downstream of the comparator 32. In the exemplary embodiment, however, the square-wave signal generated by the comparator 32 is routed directly to the phase detector 29. The phase detector 29 is embodied as an exclusive-OR gate. This is supplied, in addition to the input signal, with a feedback signal that is likewise shaped into a square-wave signal. If both square-wave signals are in the same state (e.g., both at a high or both at a low voltage level), then the output signal of the exclusive-OR gate is at a low level. If the two signals are at different levels, then the output signal is at a high level. The output signal of the phase detector is then supplied to the loop filter 30 and, via the lowpass filter 36, to the output 28. Output 28 accordingly outputs a wanted signal that was impressed onto the first carrier signal by phase modulation. The loop filter 30 is embodied as an active integrator circuit. Alternatively, a lowpass filter may be used at a very low cut-off frequency. If the two input signals of the phase detector 29 have the same frequency, then the average value of the output signal of the phase detector 29 is proportional to the phase offset between the two signals. A locking of the loop (e.g., a stable phase angle) is achieved, for example, when the input signal and the feedback signal are at the same frequency, but also when the frequency ratio is three, five, seven, etc. Downstream of the loop filter 30, a signal tap (not shown) takes place. The signal is supplied to a comparator for the purpose of determining whether the phase-locked loop circuit is locked (e.g., whether the first carrier signal is locked to the second carrier signal). In addition, the signal of the loop filter 30 is supplied to the oscillator 31 as a control signal.

The oscillator 31 may be a voltage-controlled crystal oscillator having an oscillation frequency that is variable over a narrow frequency range as a function of voltage. A virtual ground potential corresponding to the desired operating point of the phase detector, and consequently to the center point of the partially point-symmetrically extending phase detector characteristic curve, may be specified in the loop filter 30 (e.g., the active integrator). A maximum phase deviation by the modulation signal is made possible as a result of such a choice of the zero potential.

The oscillation of the crystal oscillator is output via the output 27. In addition, the output signal of the oscillator 31 is supplied via the comparator 34, which converts the output signal into a square-wave voltage as a feedback signal to the phase detector 29. Additionally arranged downstream of the comparator 34 is an inverter 37 that is controllable by the second control device 11 via the control input 38. The inverter 37 may be driven as a function of the actuation of the control element 13 as well as for transmitting identification information. An inversion of the feedback signal by the inverter 37 leads to a phase shift of the second carrier signal through 180°. The phase shift is smoothed by the phase-locked loop circuit (i.e., does not take place abruptly). Also shown in addition in FIG. 3 is the position 35 at which an additional frequency divider may be provided in an alternative embodiment.

Figure 4:
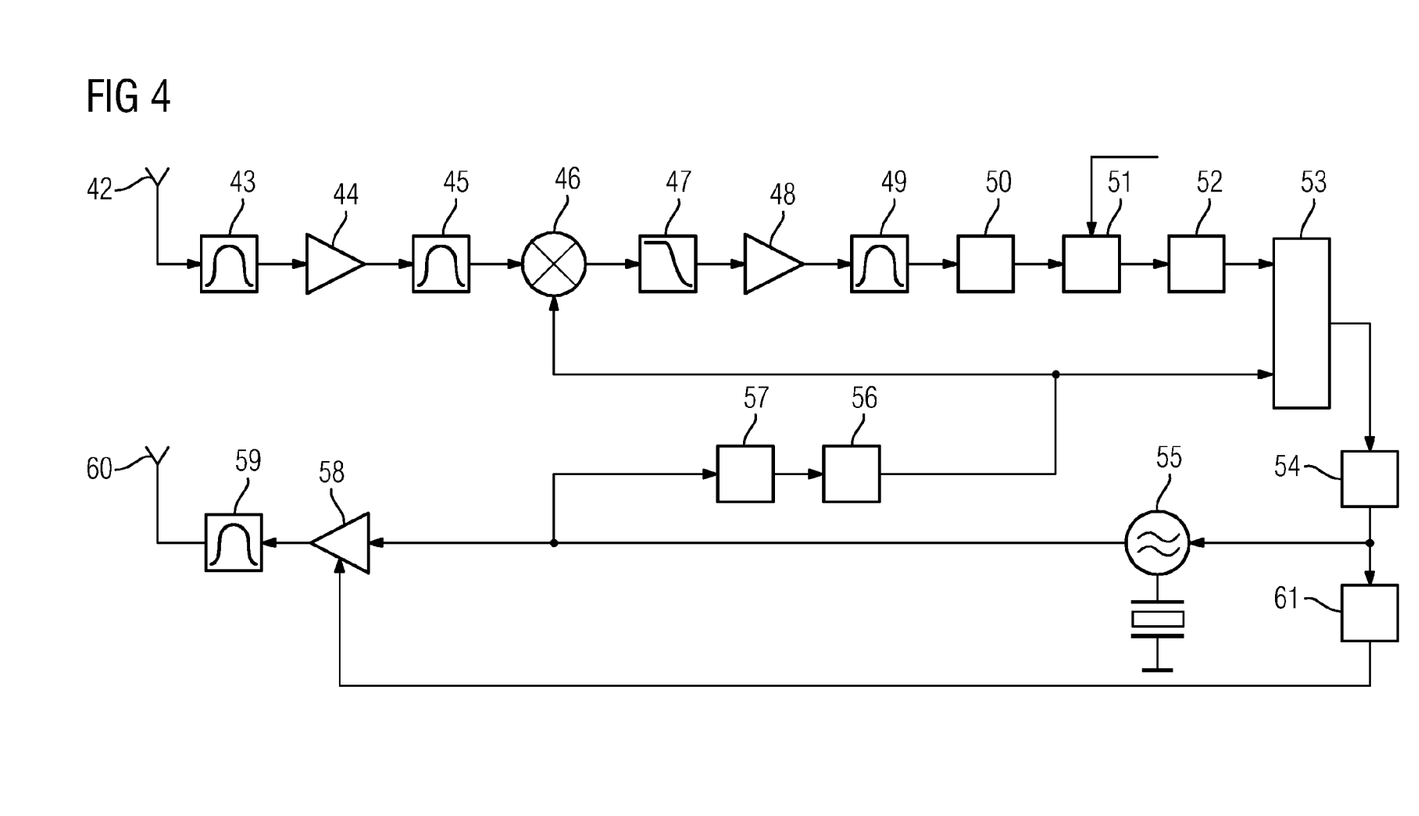
FIG. 4 shows the second communication apparatus of a second embodiment of a communication device.

FIG. 4 shows the transponder of a second communication apparatus of a further exemplary embodiment of a communication device. In this case, a carrier signal having a frequency of 25 megahertz is received by the receive antenna 42. The carrier signal next passes through a bandpass filter 43 in order to remove noise components into other frequency ranges, a non-linear amplifier 44 in order to increase the signal intensity, and a further bandpass filter 45 having a mid-band frequency of 25 megahertz. The signal level in the relevant frequency range is significantly strengthened by the non-linear amplifier 44 working in cooperation with the bandpass filters 43 and 45. The non-linearity of the non-linear amplifier 44 is of no significance here, since only the frequency and/or the phase of the received signal are/is evaluated.

The frequency of the signal preconditioned in this way is lowered by the mixer 46 and the lowpass filter 47. The amount of the frequency reduction is specified as 5 megahertz by the oscillator 55, which oscillates at 10 megahertz, and the frequency divider 56, which reduces the signal converted into a square-wave shape using the comparator 57, to half of its frequency. The signal therefore has a frequency of 20 megahertz at the input of the non-linear amplifier 48. Following the non-linear amplification, the signal is bandpass-filtered by the bandpass filter 49 around a frequency of 20 megahertz and converted by the comparator 50 into a square wave. The square-wave signal is supplied to the inverter 51, which, upon actuation of a control element (not shown), inverts the signal in order to bring about a phase shift in the output signal.

Next, the signal passes through the frequency divider 52, which reduces the frequency of the supplied square-wave signal by the factor 4, whereby, in the locked state of the loop, the frequency is equal to the frequency of the signal that is supplied to the phase detector 53 via the frequency divider 56. The output signal of the phase detector 53 is supplied to the loop filter 54, the output of which controls the frequency of the oscillator 55. The oscillation frequency of the oscillator 55 is adjusted in order to reach a state in which the output signal of the oscillator 55 is phase-locked to the first carrier signal received via the receive antenna 42. The output signal of the oscillator 55 is supplied via the amplifier 58 and the bandpass filter 59 to the transmit antenna 60. The amplifier 58 may be active only when the comparator 61 detects that the oscillator 55, and consequently the second carrier signal, is phase-locked to the first carrier signal.

The relative phase angle of the transmit signal to the first carrier signal is dependent on whether the signal is inverted by the inverter 51 or not, and consequently, on the operation of the control element. The transponder shown may therefore be used in order to communicate the operation of an individual control element from the second communication apparatus to the first communication apparatus. For example, the second communication apparatus may be used as a separately embodied call button in a magnetic resonance tomography system.

Figure 5:
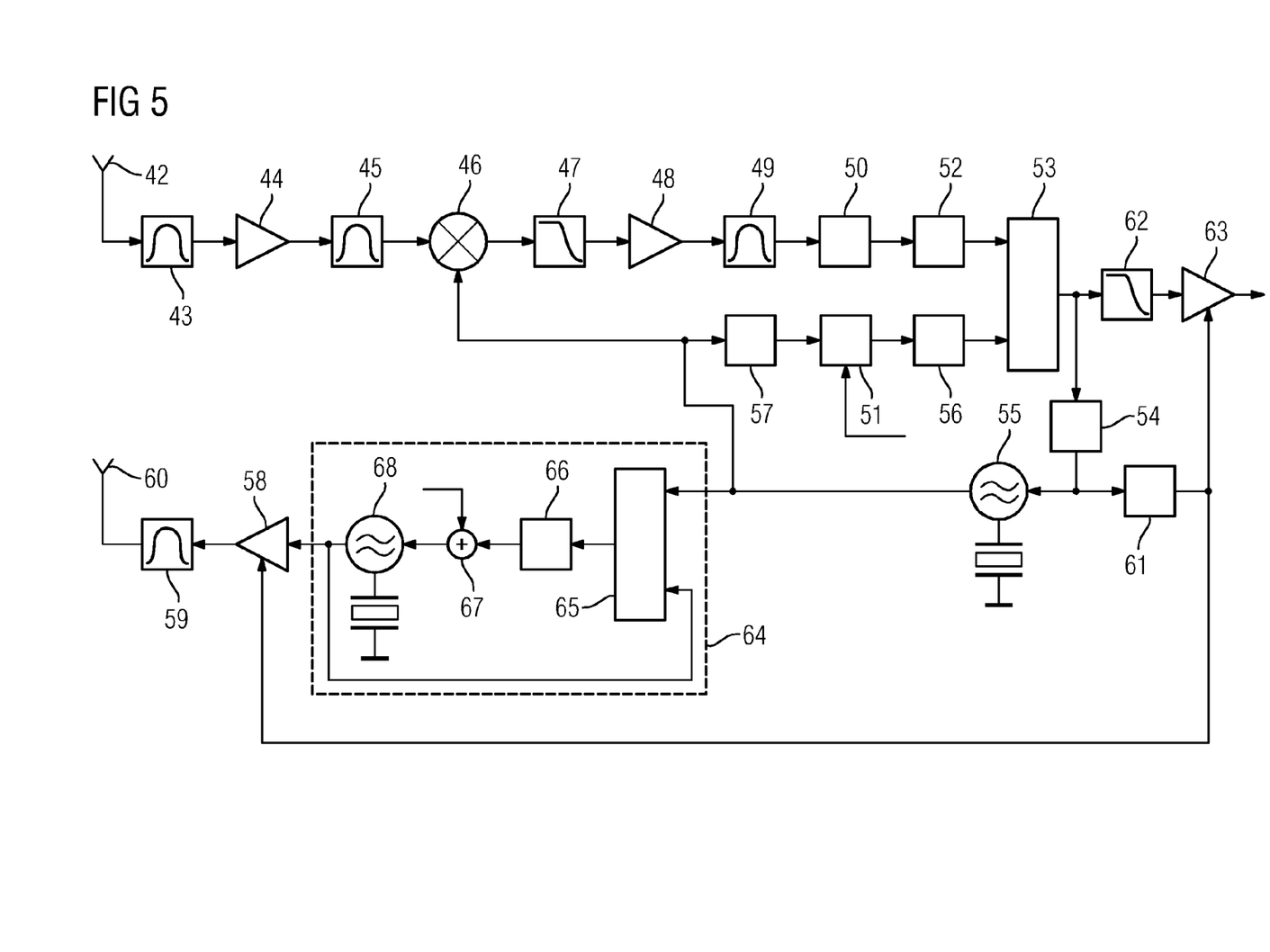
FIG. 5 shows the second communication apparatus of a third embodiment of a communication device.

FIG. 5 shows a further exemplary embodiment of a transponder in a second communication apparatus. The layout of the transponder corresponds to a large extent to that of the transponder shown in FIG. 4, where elements having the same function are labeled identically. Only the differences compared to the transponder shown in FIG. 4 are explained in the following description.

Contrary to FIG. 4, the second carrier signal provided by the oscillator 55 is in this case routed unmodified to the mixer 46. In contrast, the comparator 57 and a frequency divider 56 having the division factor 4 are provided in the feedback path to the phase detector 53. In addition, the inverter 51 is provided upstream of the frequency divider 56. This provides that the inverter 51 is arranged, not at the input of the phase-locked loop circuit, but in its feedback circuit. In a possible embodiment variant that is not shown, a signal supplied solely to the mixer may also be inverted.

The frequency divider 52 has a division factor of 1 (e.g., the frequency divider 52 allows the signal to pass through unchanged). If a first carrier signal having a frequency of 25 megahertz is supplied to the transponder shown in FIG. 5, then the frequency is converted by the mixer 46 and the filter 47 to an intermediate frequency of 5 megahertz. The oscillator accordingly generates a second carrier signal at a frequency of 20 megahertz. If, referring to FIG. 5, the division ratio of the frequency divider 52 is designated as r, and the division ratio of the frequency divider 56 as n, the frequency of the second carrier signal may be smaller by the factor $1/(1+r/n)$ than the frequency of the first carrier signal. In contrast thereto, it holds for the circuit shown in FIG. 4 that, given the same designation of the division ratios, the ratio between the frequency of the second carrier signal and the first carrier signal may be $F1/F2=n/(r+1)$. The division ratio is therefore virtually freely selectable in both circuits.

Compared to the transponder shown in FIG. 4, the transponder shown in FIG. 5 is also provided with a lowpass filter 62 and an amplifier 63 for outputting a wanted signal. If a signal received at the receive antenna 42 is one in which the first carrier signal is phase-modulated by a wanted signal in the audio range, the wanted signal is re-output via the amplifier 63. In order to avoid parasitic noise being output, the amplifier 63 is switched, like the amplifier 58, upstream of the transmit antenna 60, by the comparator 61 and is active only when the first carrier signal and the second carrier signal are phase-locked.

In order to enable audio signals to be transmitted also from the second communication apparatus to the first communication apparatus, the transponder in FIG. 5 also includes a modulation circuit 64. This modulates an audio signal of a microphone onto the second carrier frequency. For this, modulation circuit includes a second phase detector 65, a second loop filter 66, an adder 67, and a second oscillator 68. If a microphone signal (e.g., a preamplified microphone signal) is supplied to the adder 67, the audio signal is transmitted via the antenna 60 as an information signal or wanted signal that frequency-modulates the second carrier signal to the first communication apparatus, where the second carrier signal may be demodulated and output.

If an odd division ratio (e.g., three) is provided for the frequency divider 56, the transponder shown in FIG. 5 may be simplified further by dispensing with the frequency divider 56 and exploiting the fact that it is also possible to lock the phase-locked loop circuit onto higher harmonic oscillations of an input signal. By suitable choice of the frequency of the first carrier signal, of the frequency range of the oscillator 55, and/or of the filters 47, 49, the phase detector 53 may serve as a "virtual" frequency divider. This enables frequency concepts in which it is precluded on principle for harmonics of the signal frequencies involved to fall into the receive band of the first carrier signal, to which frequencies the transponder locks involuntarily ("self-locking").

Figure 6:
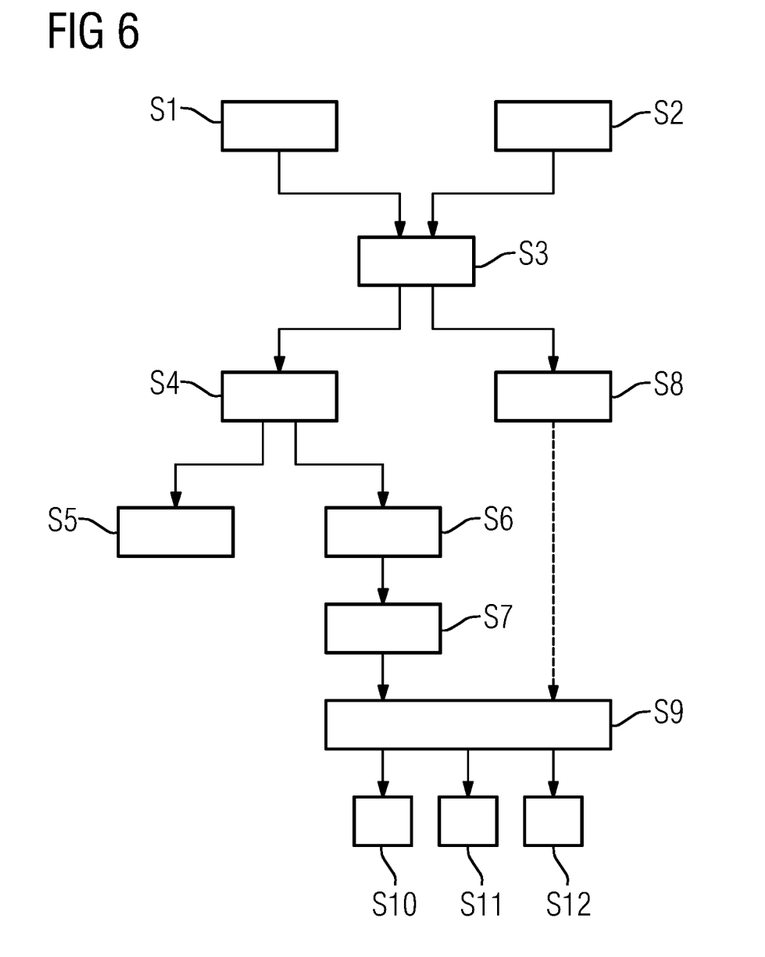
FIG. 6 shows a flowchart of an exemplary embodiment of a method.

FIG. 6 shows a communication method according to one or more of the present embodiments. In act S1, a first carrier signal is generated, and a wanted signal (e.g., a voice input) is acquired in act S2. In act S3, the wanted signal is modulated onto the first carrier signal, and the resulting signal is sent via a transmit device of a first communication apparatus. In act S4, the second communication apparatus receives the first carrier signal modulated by the further wanted signal and demodulates the signal. In act S5, the wanted signal is recovered and output, for example, as an audio signal via a loudspeaker, and in act S6, a second carrier signal is generated at a second frequency that stands in a fixed frequency ratio to the first frequency of the first carrier signal and has a fixed phase relationship to the first carrier signal. The frequency ratio between the first frequency and the second frequency is, for example, not integral. In act S7, a further wanted signal is acquired, and the fixed phase relationship between the first and second carrier signal is adjusted, and/or the second carrier signal is modulated. For example, a first wanted signal (e.g., an audio signal) may be impressed by a frequency modulation, and/or one or more additional wanted signals may be impressed by a digital switching of the phase (e.g., by an inversion of an input or feedback signal during the generation of the second carrier signal), onto the second carrier signal in order to generate a transmit signal.

In act S8, the modulated first carrier signal is received by a third communication apparatus, which may be, for example, a measurement instrument, such as an electrocardiograph. As explained with reference to acts S6 and S7, in relation to the second communication apparatus, a third carrier signal is then generated, and user information (e.g., an electrocardiogram) is modulated onto the carrier signal in order to generate a transmit signal. This is indicated by the dashed line.

In act S9, the transmit signals of the second communication apparatus and the third communication apparatus are received by the first communication apparatus and demodulated. In act S10, an audio signal previously modulated in the second communication apparatus by frequency modulation, onto the signal is then output. In act S11, the changes to the relative phase of the first carrier signal and the second carrier signal are output and provided for further systems for further processing purposes. In act S12, the data transmitted as a wanted signal by the third communication apparatus is recovered and provided for further processing.

Various possibilities for performing the individual acts are explained with reference to FIGS. 1 to 5.

Although the invention has been illustrated and described in greater detail based on the exemplary embodiments, the invention is not limited by the disclosed examples, and other variations may be derived herefrom by the person skilled in the art without leaving the scope of protection of the invention.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A communication method for communication between a first communication apparatus and a second communication apparatus, wherein at least one wanted signal is transmitted from the second communication apparatus to the first communication apparatus, the method comprising:

sending, by a transmit device of the first communication apparatus, a first carrier signal at a first frequency;

receiving, by a receive antenna of the second communication apparatus, the first carrier signal;

generating a second carrier signal at a second frequency, the generating of the second carrier signal comprising supplying a mixer of the second communication apparatus with a signal received from the receive antenna and an output signal of a phase-locked loop circuit of the second communication apparatus and supplying an output signal of the mixer to an input of the phase-locked loop circuit via a filter of the second communication apparatus, an output signal of the phase-locked loop circuit being the second carrier signal, the second frequency being different than the first frequency and having a specified rational frequency ratio with respect to the first frequency and a specified phase angle to a phase of the first carrier signal;

generating a transmit signal, the generating of the transmit signal comprising modulating, by a modulation circuit of the second communication apparatus, the second carrier signal in each case as a function of the at least one wanted signal;

sending, by a transmit antenna of the second communication apparatus, the transmit signal using the second carrier signal;

receiving, by a receive device of the first communication apparatus, the transmit signal; and recovering the at least one wanted signal, the recovering comprising demodulating, by a demodulation device of the first communication apparatus, the transmit signal.

2. The communication method of claim 1, further comprising modulating a further wanted signal onto the first carrier signal using the first communication apparatus.

3. The communication method of claim 1, further comprising:

receiving the first carrier signal by a third communication apparatus; and generating a third carrier signal at a third frequency, the third frequency being different from the first frequency and the second frequency and having a specified rational frequency ratio with respect to the first frequency and a specified phase angle with respect to the phase of the first carrier signal, wherein as a function of a third wanted signal, the third frequency, the specified phase angle of the third carrier signal, or the third frequency and the specified phase angle of the third carrier signal are varied as a function of the third wanted signal, the third carrier signal is modulated by third communication apparatus, or a combination thereof.

4. The communication method of claim 1, further comprising:

acquiring a voice input as the wanted signal using the second communication apparatus; and transmitting the voice input to the first communication apparatus; and outputting a voice signal at the first communication apparatus using a sound converter.

5. The communication method of claim 1, wherein the first frequency is chosen such that in a locked state of the phase-locked loop circuit a feedback signal supplied to a first input of a phase detector of the phase-locked loop circuit has a third frequency that is an odd integer multiple or an odd integer divider of a fourth frequency of an input signal at a second input of the phase detector.

6. The communication method of claim 1, further comprising amplifying and filtering the received first carrier signal, wherein the signal received from the receive antenna is the amplified and filtered first carrier signal.

7. A communication device comprising:

a first communication apparatus; and
a second communication apparatus,
wherein the first communication apparatus comprises:
a transmit device operable to send a carrier signal at a first frequency;
a receive device operable to receive a transmit signal of the second communication apparatus; and
a demodulation device operable to recover a wanted signal from the transmit signal, and
wherein the second communication apparatus comprises:
a receive antenna operable to receive the first carrier signal;

a transmit antenna operable to send the transmit signal using a second carrier signal that has a second frequency different from the first frequency;

a mixer, a filter, and a phase-locked loop circuit, wherein the mixer is suppliable with the receive signal and an output signal of the phase-locked loop circuit, and an output signal of the mixer is suppliable to an input of the phase-locked loop circuit via the filter, wherein the output signal of the phase-locked loop circuit is the second carrier signal and stands in a rational frequency ratio and a specified phase relationship to the first carrier signal; and a modulation circuit operable to modulate the second carrier signal as a function of the wanted signal in order to generate the transmit signal.

8. The communication device of claim 7, wherein a frequency divider is connected into a feedback circuit of the phase-locked loop circuit, upstream of the input of the phase-locked loop circuit, between the output of the phase-locked loop circuit and the mixer, or any combination thereof.

9. The communication device of claim 7, wherein a non-linear amplifier is connected between the receive antenna and the mixer, between the mixer and the phase-locked loop circuit, or a combination thereof.

10. The communication device of claim 7, wherein the phase-locked loop circuit comprises a phase detector, a loop filter, and an oscillator.

11. The communication device of claim 10, wherein the oscillator is a voltage-controlled crystal oscillator.

12. The communication device of claim 10, wherein the phase detector comprises an exclusive-OR gate.

13. The communication device of claim 10, wherein the output signal of the loop filter is supplied to a comparator, an output signal of the comparator triggering the output of the transmit signal.

14. The communication device of claim 10, wherein an inverter switched as a function of the wanted signal is connected between the output of the oscillator and the mixer, between the output of the oscillator and the phase detector, between the mixer and an input of the phase-locked loop circuit, or any combination thereof.

15. The communication device of claim 10, wherein the output signal of the loop filter or the output signal of the phase detector is supplied directly or indirectly to a sound converter.

16. The communication device of claim 7, wherein the modulation circuit is a frequency or phase modulation circuit.

17. The communication device of claim 7, wherein the second communication apparatus comprises a rechargeable energy storage device for supplying energy and a charging device for charging the energy storage device using energy of the receive signal.

18. The communication device of claim 7, wherein the first communication apparatus comprises:

a charging device operable to receive the second communication apparatus; and a transmit power control device operable to increase the transmit power of the carrier signal when the second communication apparatus is received in the charging device.

19. The communication device of claim 7, wherein the second communication apparatus comprises a magnetic field detector operable to detect a magnetic field, wherein a transmission of the transmit signal is switchable as a function of a detected magnetic field.

20. The communication device of claim 19, wherein the magnetic field detector comprises a Hall probe.

21. The communication device of claim 7, wherein a control device of the second communication apparatus is operable to send a stored identification signal as the wanted signal when an identification condition occurs.

22. A magnetic resonance tomography system comprising:
 a communication device comprising:
  a first communication apparatus; and
  a second communication apparatus,
 wherein the first communication apparatus comprises:
  a transmit device operable to send a carrier signal at a first frequency;
  a receive device operable to receive a transmit signal of the second communication apparatus; and
  a demodulation device operable to recover a wanted signal from the transmit signal, and
 wherein the second communication apparatus comprises:
  a receive antenna operable to receive the first carrier signal;
  a transmit antenna operable to send the transmit signal using a second carrier signal that has a second frequency different from the first frequency;
  a mixer, a filter, and a phase-locked loop circuit, wherein the mixer is suppliable with the receive signal and an output signal of the phase-locked loop circuit, and an output signal of the mixer is suppliable to an input of the phase-locked loop circuit via the filter, wherein the output signal of the phase-locked loop circuit is the second carrier signal and stands in a rational frequency ratio and a specified phase relationship to the first carrier signal; and
  a modulation circuit operable to modulate the second carrier signal as a function of the wanted signal in order to generate the transmit signal.

23. A communication method for communication between a first communication apparatus and a second communication apparatus, wherein at least one wanted signal is transmitted from the second communication apparatus to the first communication apparatus, the method comprising:
 sending a first carrier signal at a first frequency using the first communication apparatus;
 receiving the first carrier signal by the second communication apparatus and generating a second carrier signal at a second frequency, the second frequency being different than the first frequency and having a specified rational frequency ratio with respect to the first frequency and a specified phase angle to a phase of the first carrier signal;
 changing the second frequency, the specified phase angle, or the second frequency and the specified phase angle, modulating the second carrier signal in each case as a function of the wanted signal in order to generate a transmit signal and sending the transmit signal using the second communication apparatus, or a combination thereof; and
 receiving the transmit signal and demodulating the transmit signal in order to recover the wanted signal using the first communication apparatus,
 wherein a communication apparatus having a phase-locked loop circuit for generating the second carrier signal is used as the second communication apparatus, and
 wherein the first frequency is chosen such that in a locked state of the phase-locked loop circuit a feedback signal supplied to a first input of a phase detector of the phase-locked loop circuit has a third frequency that is an odd integer multiple or an odd integer divider of a fourth frequency of an input signal at a second input of the phase detector.

* * * * *